United States Patent [19]

Kuwata et al.

[11] Patent Number: 4,720,464
[45] Date of Patent: Jan. 19, 1988

[54] ELECTROLYTES FOR KARL FISCHER COULOMETRIC TITRATION

[75] Inventors: Sinichi Kuwata, Machida; Hiromasa Katoh, Hachiouji; Mitsumasa Ono, Ebina, all of Japan

[73] Assignee: Mitsubishi Chemical Industries, Limited, Tokyo, Japan

[21] Appl. No.: 674,589

[22] Filed: Nov. 26, 1984

[30] Foreign Application Priority Data

Dec. 28, 1983 [JP] Japan .................... 58-248005
May 7, 1984 [JP] Japan .................... 59-90432

[51] Int. Cl.$^4$ ............................. G01N 33/18
[52] U.S. Cl. ............................. 436/42; 204/1 T
[58] Field of Search ............. 436/39, 42; 204/1 T, 204/1 M

[56] References Cited

U.S. PATENT DOCUMENTS 3,656,907  4/1972  Delmonte ................. 436/42
4,368,105  1/1983  Muroi et al. ............. 204/1 M
4,378,972  4/1983  Scholz .................... 436/42

FOREIGN PATENT DOCUMENTS 0094065  5/1984  Japan .................... 436/42

OTHER PUBLICATIONS

Mitsubishi, Chemical Abstracts, vol. 101, 1984, p. 578, No. 101:239567f.

Primary Examiner—Barry S. Richman
Assistant Examiner—Robert J. Hill, Jr.
Attorney, Agent, or Firm—Jordan B. Bierman

[57] ABSTRACT

An electrolyte for Karl Fischer coulometric titration, which contains
(a) iodine or an iodine compound,
(b) sulfur dioxide,
(c) a halogenated hydrocarbon or an aromatic hydrocarbon,
and
(d)
  (i) an amine of the following general formula (I), an amine of the following general formula (II) and a monohydric alcohol, or
  (ii) an amine of the following general formula (I) and/or an amine of the following general formula (II) and a polyhydric alcohol or an ether compound thereof of the following general formula (III):

General formula (I):

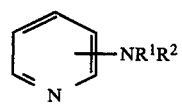

wherein $R^1$ and $R^2$ each represent a hydrogen atom, an alkyl group, a pyridyl group or a pyrrolidinyl group;

General formula (II):

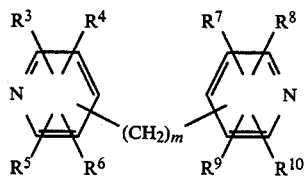

wherein $R^3$–$R^{10}$ each represent a hydrogen atom or an alkyl group, and m is an integer of 1–5;

General formula (III):

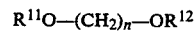

wherein $R^{11}$ and $R^{12}$ each represent a hydrogen atom or an alkyl group, and n is 2 or 3. The electrolytes of the invention are free from pungent pyridine odors and can accurately measure the water in various samples, especially those containing ketones, carboxylic acids etc.

7 Claims, 1 Drawing Figure

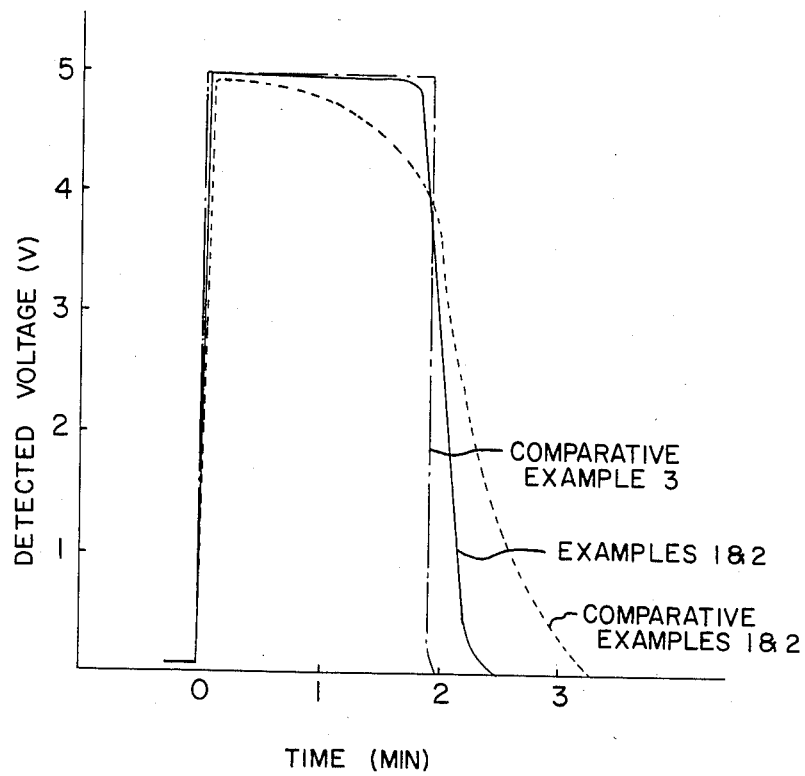

ELECTROLYTES FOR KARL FISCHER COULOMETRIC TITRATION

BACKGROUND OF THE INVENTION

1. Field of the Invention

This invention relates to electrolytes for Karl Fischer coulometric titrations, and more specifically, it relates to electrolytes for Karl Fischer coulometric titrations free from disagreeable odors and having improved functions.

2. Description of the Prior Art

Karl Fischer coulometric titration methods are known, and as electrolytes, those chiefly comprising iodine, sulfur dioxide, pyridine and methanol are generally employed. On actual measurement, iodine is present as iodide ions, and when a sample is introduced, iodine is simultaneously generated by electrolysis, thereby the Karl Fischer reaction proceeds. Therefore, electrolytes utilizing potassium iodide or sodium iodide instead of the iodine are also used.

Since conventional electrolytes for Karl Fischer coulometric titrations have contained pyridine having specific odors as one of their components, analytical operations have been inconvenient. Therefore, electrolytes free from pyridine odors have been desired. Further, in general, electrolytes for Karl Fischer coulometric titrations use methanol as a main solvent in order to easily dissolve a sample and so that the Karl Fischer reaction proceeds more quantitatively. However, where a ketone, such as acetone etc., or a carboxylic acid, such as acetic acid etc., is present in a sample, the aforesaid methanol and the ketone or the carboxylic acid react as shown in the following formulae:

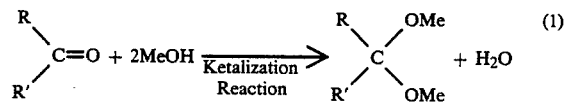

(Ketone)    (Methanol)

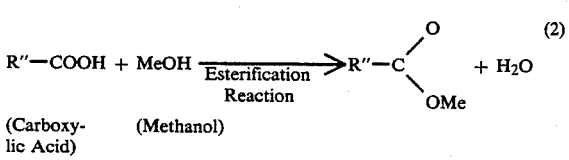

(Carboxylic Acid)    (Methanol)

wherein R, R' and R" each represent an alkyl group, to generate water, and thus interferring with the water measurement. In order to avoid such interfering reactions, there may be contemplated a method of conducting water measurement at low temperatures, but even at low temperatures, it is impossible to completely inhibit said reactions and thus the obtained results would lack accuracy. Therefore, the electrolytes for Karl Fischer coulometric titrations using methanol as a main solvent were not suitable for water measurement in ketones, carboxylic acids or samples containing them, and the advent of an electrolyte which may easily be applied to samples containing ketones etc. has been sought. Recently, as electrolytes free from pyridine odors, electrolytes using various aliphatic amines, heterocyclic compounds etc., instead of the pyridine have been proposed (Japanese Patent Application Laid-open No. 137250/1981).

On the other hand, as an electrolyte, an electrolyte in which the reaction rate for the Karl Fischer reaction is higher is desirable from the aspect that the titration time may be shortened, and an electrolyte in which the change in electric potential near the titration end point is mild is desirable from the aspect that the control of the equipment is easy and also the measurement accuracy may be improved. However, the above-described known electrolytes have not been always satisfactory from this viewpoint.

Furthermore, as electrolytes for samples containing ketones, electrolytes using chloroform and an alkylene carbonate as a main solvent have been proposed (Japanese Patent Application Laid-open No. 112641/1981). However, further improvement has been sought from the viewpoint that they have pyridine odors.

The present inventors have further continued their study for the purpose of presenting electrolytes for Karl Fischer coulometric titration which satisfy the above-described requirements, and have discovered that by using specific amines and further by selecting a specific solvent, the aimed object may be achieved, thereby having accomplished this invention.

SUMMARY OF THE INVENTION

An object of this invention is to provide electrolytes for Karl Fischer coulometric titrations which are free from pyridine odors and have a high reaction rate and in which the change in electric potential near the titration end point is mild.

Another object of this invention is to provide electrolytes for Karl Fischer coulometric titrations free from pyridine odors which can measure water even in ketones, carboxylic acids or samples containing them with good accuracy.

Accordingly, the gist of this invention resides in an electrolyte for Karl Fischer coulometric titration, which contains (a) iodine or an iodine compound,
(b) sulfur dioxide,
(c) a halogenated hydrocarbon or an aromatic hydrocarbon,
and
(d)
  (i) an amine of the following general formula (I), and amine of the following general formula (II) and a monohydric alcohol, or
  (ii) an amine of the following general formula (I) and/or an amine of the following general formula (II) and a polyhydric alcohol or an ether compound thereof of the following general formula (III):

General formula (I):

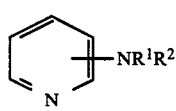

wherein $R^1$ and $R^2$ each represent a hydrogen atom, an alkyl group, a pyridyl group or a pyrrolidinyl group;

General formula (II):

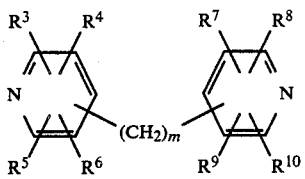

wherein $R^3$–$R^{10}$ each represent a hydrogen atom or an alkyl group, and m is an integer of 1–5;
General formula (III):

wherein $R^{11}$ and $R^{12}$ each represent a hydrogen atom or an alkyl group, and n is 2 or 3.

BRIEF DESCRIPTION OF THE DRAWING

FIG. 1 is a graph showing the change with time in the detected voltage in coulometric titration in Examples 1, 2 and Comparative Examples 1–3, in which the solid line is for the electrolytes of this invention (Examples 1 and 2), the broken line for the electrolytes utilizing pyridine or 1,3-di-(2-pyridyl)propane alone (Comparative Examples 1 and 2) and a dot-and-chain line for the electrolyte utilizing imidazole (Comparative Example 3).

DETAILED DESCRIPTION OF THE INVENTION

As the (a) iodine or iodine compound used in this invention, hydroiodic acid, potassium iodide, sodium iodide etc. are suitable. The concentration of the iodine or iodide ions in the electrolyte is suitably in the range of 0.1–4% by weight, preferably 0.3–2% by weight, calculated as the iodine.

The concentration of the (b) sulfur dioxide exerts a great influence on the reaction rate together with the basicity of the amine or amines, and even when an amine or amines having low basicity are used, the reaction rate may be increased by raising the concentration of the sulfur dioxide. As the concentration in the electrolyte, a range of 0.3–12% by weight is generally used, preferably 1.2–6% by weight.

Examples of the (c) halogenated hydrocarbon or aromatic hydrocarbon include chloroform, 1,1,1-trichloroethane, xylene etc., among which chloroform is preferred because it has a great dissolving power on various substances and has an effect to promote the Karl Fischer reaction.

The concentration of the halogenated hydrocarbon or aromatic hydrocarbon used in the electrolyte is generally in the range of 10–85% by weight, but in the case where a sample contains a ketone etc., it is advised to select 30–85% by weight, and in the case of other general samples, 10–50% by weight is recommended.

The amines in the component (d) of this invention are of the following general formulae (I) and (II):
General formula (I):

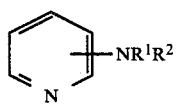

wherein $R^1$ and $R^2$ each represent a hydrogen atom, an alkyl group, a pyridyl group or a pyrrolidinyl group;
General formula (II):

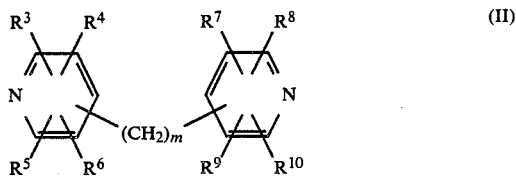

wherein $R^3$–$R^{10}$ each represent a hydrogen atom or an alkyl group, and m is an integer of 1–5. Specific examples thereof include 2-dimethylaminopyridine, 4-dimethylaminopyridine, 2-diethylaminopyridine, 2-methylaminopyridine, 2,2'-dipyridylamine, 1,3-di-(2-pyridyl)propane, 1,3-di-(4-pyridyl)propane etc.

Examples of the monohydric alcohol in the component (d) include methanol, ethanol, isopropanol etc. Examples of the polyhydric alcohol or ether compound thereof include those of the following general formula (III):
General formula (III):

wherein $R^{11}$ and $R^{12}$ each represent a hydrogen atom or an alkyl group, and n is 2 or 3. Specific examples thereof include ethylene glycol monomethyl ether, propylene glycol monomethyl ether, ethylene glycol etc.

Where this invention is applied to a sample containing a ketone or a carboxylic acid, the component (d) to be used is a combination of an amine of the above general formula (I) and/or an amine of the above general formula (II) and a polyhydric alcohol or an ether compound thereof of the above general formula (III). At that time, the concentration of the amines, as the molar ratio of the total amines to the sulfur dioxide, is suitably in the range of 0.3:1 to 6:1, preferably in the range of 0.5:1 to 3:1.

In this invention, the use in combination of the amine of the general formula (I) and the amine of the general formula (II) is preferred, because the pungent odors of the sulfur dioxide are lowered and the reaction rate is further improved. The proportion of the amine of the general formula (I) to the amine of the general formula (II) in molar ratio is in the range of 0.3–10, preferably in the range of 1–3.

The concentration of the polyhydric alcohol or ether compound thereof is suitably 5–50% by weight, preferably 10–30% by weight, since if it is too high, the ketalization reaction etc. proceed and hence accurate water measurement is difficult, whereas if it is too low, the electrolysis does not quantitatively proceed and the titration time is also lengthened.

On the other hand, where applied to a sample containing no ketone or carboxylic acid, the amines of the general formulae (I) and (II) and the monohydric alcohol are used in combination.

The concentration of the amines, as the molar ratio of the total amines to the sulfur dioxide, is suitably in the range of 0.3:1 to 6:1, preferably in the range of 0.5:1 to 3:1. The proportion of the amine of the general formula (I) to the amine of the general formula (II) in molar ratio is suitably in the range of 0.3–10, preferably in the range of 1-3, and the concentration of the monohydric alcohol is preferably in the range of 30-70% by weight.

Water determination using the electrolytes according to this invention is conducted in the conventional manner. More specifically, the electrolyte according to this invention is added to an anode chamber, an appropriate catholyte is added to a cathode chamber, and an electric current is applied, whereby the water in the anolyte is removed. Then, a sample is added to the anode chamber, an electric current is applied again, and the water in the sample is titrated. Where iodine is employed in the preparation of the anolyte, water is added until the iodine color disappears before the sample measurement. As the catholyte, a mixed solution consisting of, for example, 65% by weight of ethylene glycol monomethyl ether or methanol, 20% by weight of carbon tetrachloride, 5% by weight of sulfur dioxide and 10% by weight of 4-dimethylaminopyridine is appropriate.

This invention is more specifically described by the following examples, but this invention should not be restricted to these examples.

EXAMPLE 1

8.8 g of 4-dimethylaminopyridine, 8.7 g of 1,3-di-(2-pyridyl)propane, 0.64 g of iodine, 5.1 g of sulfur dioxide and 37 g of chloroform were dissolved in methanol and the total volume was made 100 ml. The electrolyte thus prepared was added to an anode chamber of a commercially available Karl Fischer coulometric titrator (Moisture Meter Model CA-02, manufactured by Mitsubishi Chemical Industries, Ltd.). A mixed solution consisting of 65% by weight of methanol, 20% by weight of carbon tetrachloride, 5% by weight of sulfur dioxide and 10% by weight of 4-dimethylaminopyridine was added to a cathode chamber. Thereafter, following the operations of the aforesaid coluometric titrator, 100 μl of a standard solution of water-methanol (20 mg $H_2O$/ml) was injected, and the $H_2O$ measured value and the time required to measure were determined. The results are shown in Table 1. The change with time in the detected voltage at that time is shown in FIG. 1.

EXAMPLE 2

An electrolyte was prepared in a manner similar to that in Example 1 except that the 4-dimethylaminopyridine was replaced by 7.8 g of 2-methylaminopyridine and the 1,3-di-(2-pyridyl)propane was replaced by 8.7 g of 1,3-di-(4-pyridyl)propane, and the $H_2O$ measured value and the time required to measure were determined. The results are shown in Table 1. The change with time in the detected voltage at that time is shown in FIG. 1.

COMPARATIVE EXAMPLE 1

The $H_2O$ measured value and the time required to measure were determined in a manner similar to that in Example 1 except that the electrolyte was replaced by a commercially available electrolyte utilizing pyridine as the amine (trade name: Aquamicron A, produced by Mitsubishi Chemical Industries, Ltd.). The results are shown in Table 1. The change with time in the detected voltage at that time is shown in FIG. 1.

COMPARATIVE EXAMPLE 2

As electrolyte was prepared in a manner similar to that in Example 1 except that 19.8 g of 1,3-di-(2-pyridyl)propane was used as the amine, and the $H_2O$ measured value and the time required to measure were determined. The results are shown in Table 1. The change with time in the detected voltage at that time is shown in FIG. 1.

COMPARATIVE EXAMPLE 3

The $H_2O$ measured value and the time required to measure were determined in a manner similar to that in Example 1 except that the electrolyte was replaced by a commerically available electrolyte utilizing imidazole as the amine (trade name: Hydranal-Coulomat A produced by Riedel-de Haën, West Germany). The results are shown in Table 1. The change with time in the detected voltage at that time is shown in FIG. 1.

TABLE 1

| | Apparent pH of Electrolyte | Amount of $H_2O$ Added (μg) | $H_2O$ Measured Value (μg) | Time Required to Measure |
|---|---|---|---|---|
| Example 1 | 5.2 | 2000 | 2009 | 2 min 10 sec. |
| Example 2 | 4.4 | 2000 | 2010 | 2 min 20 sec. |
| Comparative Example 1 | 4.0 | 2000 | 2005 | 3 min 00 sec. |
| Comparative Example 2 | 3.7 | 2000 | 2010 | 2 min 40 sec. |
| Comparative Example 3 | 6.2 | 2000 | 2008 | 1 min 50 sec. |

It can be recognized from Table 1 that by the electrolytes of this invention, coulometric titration may be effected with high measurement accuracy and in an extremely shortened measuring time. In the case of the electrolyte utilizing imidazole as the amine (Comparative Example 3), although the measuring time is as short as 1 minute 50 seconds as shown in FIG. 1, since the change in the electric potential near the titration end point is too rapid and hence overtitration is apt to occur, there is the problem that it is difficult to control the measurement.

As has been described in detail above, the electrolytes for Karl Fischer coulometric titration according to this invention are free from disagreeable or pungent odors such as pyridine odors etc. and also have a high reaction rate and thus the time required to measure is shortened, and moreover, since the change in the electric potential near the titration end point is mild, the control of the measurement is easy. Therefore, by the electrolytes of this invention, Karl Fischer coulometric titration may be easily effected with high accuracy in a short time and the operational atmosphere for titration is also good.

EXAMPLE 3

A solution obtained by dissolving 7.4 g of 4-dimethylaminopyridine, 5.9 g of 1,3-di-(2-pyridyl)propane, 3.8 g of sulfur dioxide, 2.5 g of iodine and 25 ml of ethylene glycol monomethyl ether in chloroform and making the total volume 100 ml was added to an anode chamber of a commercially available Karl Fischer coulometric titrator (Moisture Meter Model CA-02, manufactured by Mitsubishi Chemical Industries, Ltd.).

To a cathode chamber was added a mixed solution consisting of 65% by weight of ethylene glycol monomethyl ether, 20% by weight of carbon tetrachloride, 5% by weight of sulfur dioxide and 10% by weight of 4-dimethylaminopyridine. Thereafter, according to the operations of the aforesaid coulometric titrator, a commercially available acetone was injected in 1 ml portions, and the water in the acetone was measured. The results are shown in Table 2. Similarly, the water in commercially available acetic acid and dichloroacetic acid was measured. The results are also shown in Table 2.

EXAMPLE 4

A solution obtained by dissolving 6.2 g of 4-dimethylaminopyridine, 5.9 g of 1,3-di-(2-pyridyl)propane, 3.8 g of sulfur dioxide, 1.3 g of iodine, 15 ml of ethylene glycol monomethyl ether and 30 ml of propylene glycol monomethyl ether in chloroform and making the total volume 100 ml was used to measure the water in acetone in a manner similar to that in Example 3. The results are shown in Table 2.

EXAMPLE 5

A solution obtained by dissolving 7.4 g of 4-dimethylaminopyridine, 5.9 g of 1,3-di-(2-pyridyl)propane, 3.8 g of sulfur dioxide, 1.3 g of iodine and 25 ml of ethylene glycol monobutyl ether in chloroform and making the total volume 100 ml was used to measure the water in acetone in a manner similar to that in Example 3. It was possible to measure water with good accuracy in samples containing up to 5 ml of acetone.

EXAMPLE 8

A solution obtained by dissolving 14.8 g of 2-dimethylaminopyridine, 3.8 g of sulfur dioxide, 2.5 g of iodine and 25 ml of ethylene glycol monomethyl ether in chloroform and making the total volume 100 ml was used to measure the water in acetone in a manner similar to that in Example 3. It was possible to measure water with good accuracy in samples containing up to 15 ml of actone.

COMPARATIVE EXAMPLE 4

The water in acetone and dichloroacetic acid was measured in a manner similar to that in Example 3 except that the ethylene glycol monomethyl ether in Example 3 was replaced by methanol. The results are shown in Table 2.

The electrolytes for Karl Fischer coulometric titrations of this invention are free from disagreeable odors and may be advantageously used to measure the water in ketones, carboxylic acids or samples containing ketones and carboxylic acids.

TABLE 2

| Sample | Example 3 | | | Example 4 | Comparative Example 4 | |
| --- | --- | --- | --- | --- | --- | --- |
| | Acetone | Acetic Acid | Dichloroacetic Acid | Acetone | Acetone | Dichloroacetic Acid |
| Measured Value of Water in 1 ml of Sample (μg) (Measurement repeated predetermined times using the same electrolyte) | 1517 | 688 | 1314 | 1528 | Not measurable (Due to water generated measurable conditions of the device were exceeded) | Not measurable (Same as the left) |
| | 1510 | 696 | 1314 | 1495 | | |
| | 1515 | 693 | 1321 | 1494 | | |
| | 1507 | 696 | 1306 | 1499 | | |
| | 1490 | 698 | 1293 | 1472 | | |
| | 1479 | 698 | 1310 | 1494 | | |
| | 1478 | 695 | 1292 | 1483 | | |
| | 1468 | 694 | 1359 | 1488 | | |
| | 1475 | 699 | 1307 | | | |
| | 1475 | 695 | | | | |
| | 1455 | 678 | | | | |
| | 1479 | 682 | | | | |
| | 1464 | 691 | | | | |
| | 1455 | 675 | | | | |
| | 1483 | 679 | | | | |
| Average (μg) Value | 1483 | 690 | 1313 | 1494 | — | — |
| Coefficient of variation(*) | 1.4% | 1.2% | 1.5% | 1.1% | — | — |

$$(*)\frac{\sqrt{\frac{\Sigma(x_i - \bar{x})^2}{n - 1}}}{\bar{x}} \times 100$$

$x_i$: measured value at the i-th time;
$\bar{x}$: average value of the measured values;
n: measured times

EXAMPLE 6

A solution obtained by dissolving 7.4 g of 4-dimethylaminopyridine, 5.9 g of 1,3-di-(2-pyridyl)propane, 3.8 g of sulfur dioxide, 2.5 g of iodine and 25 ml of ethylene glycol in chloroform and making the total volume 100 ml was used to measure the water in acetone in a manner similar to that in Example 3. It was possible to measure water with good accuracy in samples containing up to 3 ml of acetone.

EXAMPLE 7

A solution obtained by dissolving 10.3 g of 2,2'-dipyridylamine, 5.9 g of 1,3-di-(2-pyridyl)propane, 3.8 g of sulfur dioxide, 2.5 g of iodine and 25 ml of ethylene glycol monomethyl ether in chloroform and making the total volume 100 ml was used to measure the water in acetone in a manner similar to that in Example 3. It was

What is claimed is:

1. An electrolyte for Karl Fischer Coulometric titration which contains effective amounts of
  A. iodine or an iodine compound
  B. SO₂
  C. a halogenated hydrocarbon or an aromatic hydrocarbon, and
  D. an amine component
  wherein said amine component is taken from Class 1 or Class 2 wherein Class 1 consists of:
    (i) a first amine of Formula I,
    (ii) a second amine of Formula II, wherein the molar ratio of said first amine to said second amine is in the range of 0.3 to 10, and
    (iii) 30 to 70 weight % of a monohydric alcohol, or 5 to 50 weight % of a polyhydric alcohol or an ether compound thereof of Formula III wherein Class 2 consists of:
 (i) said first amine or said second amine and
 (ii) 5 to 50 weight % of said polyhydric alcohol or said ether compound thereof,
wherein the weight percentages are based on said electrolyte, wherein the molar ratio of total amines to sulfur dioxide in the electrolyte is from 0.3:1 to 6:1, and wherein Formula I is:

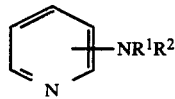  (I)

wherein $R^1$ and $R^2$ each represents a hydrogen atom, an alkyl group, a pyridyl group or a pyrrolidinyl group;
Formula II is:

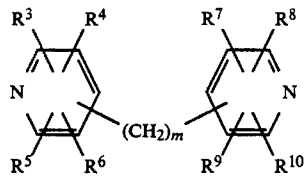  (II)

wherein $R^3$ to $R^{10}$ each represents a hydrogen atom or an alkyl group, and m is an integer of 1 to 5; and
Formula III is:

$$R^{11}O-(CH_2)_n-OR^{12} \qquad (III)$$

wherein $R^{11}$ and $R^{12}$ each represents a hydrogen atom or an alkyl group, an n is 2 or 3.

2. The electrolyte of claim 1 wherein said first amine is 4-dimethylaminopyridine and said second amine is 1,3-di-(2-pyridyl)propane.

3. The electrolyte of claim 1 wherein said first amine is 2-methylaminopyridine and said second amine is 1,3-di-(4-pyridyl)propane.

4. The electrolyte of claim 1 wherein said first amine is 4-dimethylaminopyridine, said second amine is 1,3-di-(2-hyridyl)-propane, and Formula III is ethylene glycol monomethyl ether.

5. The electrolyte of claim 1 wherein said amine component is taken from Class 1.

6. The electrolyte of claim 1 wherein Class 1 (iii) consists of:
 said polyhydric alcohol or said ether compound thereof.

7. The electrolyte of claim 1 wherein said amine component includes a combination of the amines of Formula I and II, and a monohydric or polyhydric alcohol.

* * * * *